United States Patent [19]
Hodgkinson

[11] Patent Number: 5,898,082
[45] Date of Patent: Apr. 27, 1999

[54] PROCESS FOR THE PREPARATION OF N-PHOSPHONOMETHYLGLYCINE

[75] Inventor: Ian Hodgkinson, Holmbridge, United Kingdom

[73] Assignee: Zeneca Limited, United Kingdom

[21] Appl. No.: 08/983,112

[22] PCT Filed: Jun. 27, 1996

[86] PCT No.: PCT/GB96/01548

§ 371 Date: Jan. 8, 1998

§ 102(e) Date: Jan. 8, 1998

[87] PCT Pub. No.: WO97/05149

PCT Pub. Date: Feb. 13, 1997

[30] Foreign Application Priority Data

Jul. 25, 1995 [GB] United Kingdom .................... 9515265

[51] Int. Cl.$^6$ ...................................................... C07F 9/22
[52] U.S. Cl. ................................................................ 562/17
[58] Field of Search ................................................ 562/17

[56] References Cited

U.S. PATENT DOCUMENTS

| | | | |
|---|---|---|---|
| 4,033,896 | 7/1977 | Mitchell et al. | 252/389 |
| 4,079,006 | 3/1978 | Mitchell | 210/58 |
| 5,087,740 | 2/1992 | Smith | 562/17 |

OTHER PUBLICATIONS

Subramaniam et al., 'Metal Complexes of Glyphosate', J. Agric. Food Chem., vol. 36, No. 6, 1988, pp. 1326–1329.
McBride, M. et al.: Soil Sci. Soc. Am. J. 53:1668–1673 (1989).
Piccolo, A. et al, CA 117:228347 (1992).
Zykova, G.V. et al., CA 112:11673 (1989).
Nilsson, G., CA 91:51017 (1979).
Hensley, D.L. et al., CA 90:49511 (1978).
Dhansay, M.A. et al., CA 120:16661 (1993).
Subramaniam, V. et al., CA 109:196680 (1988).
Motekaitis, R. et al., CA 104:25036 (1985).
Glass, R.L., CA 101:205947 (1984).
Madsen, H.E.L. et al., CA 88:142427 (1978).

*Primary Examiner*—Brian M. Burn
*Assistant Examiner*—Brian J. Davis
*Attorney, Agent, or Firm*—David P. LeCroy

[57] ABSTRACT

A process for removing N-(phosphonomethylglycine) (glyphosate) or a salt or ionic form thereof from an aqueous mixture in which it is present, wherein the aqueous mixture is an effluent from a glyphosate manufacturing process, the process comprising adding to the mixture of ions capable of forming an insoluble or partially soluble complex glyphosate salt, and removing the complex salt from the mixture. An additional process permits recovery of glyphosate from the precipitate of complex salts by a process comprising forming an aqueous slurry of the precipitate having a pH greater than 8 and removing the resultant metal oxide from the slurry to give an aqueous solution containing glyphosate.

11 Claims, No Drawings

PROCESS FOR THE PREPARATION OF N-PHOSPHONOMETHYLGLYCINE

The present invention relates to processes for the preparation of N-phosphonomethylglycine (glyphosate), a broad spectrum herbicide which is widely used throughout the world. In particular, the invention relates to a means of reducing the amount of glyphosate which is expelled with the effluent from the manufacturing processes.

There are several well known manufacturing routes by which glyphosate can be prepared, for example the routes set out in U.S. Pat. No. 3,969,398, U.S. Pat. No. 3,799,758, U.S. Pat. No. 3,927,080, U.S. Pat. No. 4,237,065 and U.S. Pat. No. 4,065,491, but all of these routes have a common problem. This is that, however efficient the process, there will usually be some wastage of product. Potentially, the presence of glyphosate in effluent can present environmental problems because of its herbicidal properties.

Wastage of product is, of course, also undesirable from the point of view of the manufacturer who wishes to produce glyphosate as economically as possible and so, for all of these reasons, it is essential that as little of the product as possible is expelled with effluent from the plant.

EP-A-0323821 addresses the problem of treating the waste stream from a glyphosate plant and suggests the solution of contacting the waste stream with a transition metal catalyst in a mixture or solution. The mixture or solution must be contacted with a molecular oxygen-containing gas and the reaction mass heated to a sufficient temperature to initiate and sustain the oxidation reactions of phosphonomethylglycine derivatives. This process has the disadvantage, however, that it is expensive since the catalyst, the contacting with the molecular oxygen containing gas and the heating all add to the cost. In addition, the reaction must often be conducted at elevated pressure which, again, increases the costs of the treatment process.

The present invention relates to an efficient and cost effective process for removing glyphosate or a salt or derivative thereof from a mixture in which it is present wherein the mixture is the effluent from a glyphosate manufacturing process.

In a first aspect of the present invention there is provided a process for removing N-(phosphonomethylglycine) (glyphosate) or a salt or ionic form thereof from an aqueous mixture in which it is present, wherein the aqueous mixture is an effluent from a glyphosate manufacturing process, the process comprising adding to the mixture ions capable of forming an insoluble or partially soluble complex glyphosate salt, and removing the complex salt from the mixture.

Examples of water soluble salts of glyphosate include the sodium (for example monosodium and disodium salts), potassium, ammonium, trimethylsulfonium and isopropylammonium salts. Ionic forms of glyphosate include the protonated form or the zwitterion.

When the ions are added to an aqueous mixture containing glyphosate, the present inventors have discovered that a complex salt appears to form. The complex salt is insoluble in water and precipitates out of solution. The ions added to the mixture may be iron (III), calcium, magnesium or aluminium ions. However, iron (III) ions are preferred since they form the least soluble complex salts which are, therefore, most easily removed.

The formation and/or the solubility of the complex salt may be pH dependent and, usually, acid or neutral conditions may be required. In the case of iron (III) the pH of the glyphosate-containing mixture may be adjusted to pH 6 or less before the addition of the iron (III) salt. It is preferred that the pH is from 1 to 4, for example about pH 3.

The ions which are added to the glyphosate-containing mixture will preferably be added in the form of a water soluble salt. Since, as mentioned above, the formation of the complex salt appears to be pH dependent, the salt should be one which is soluble in acidic solutions, for example of pH 5 or less. In the case of iron (III) the soluble salt may be, for example, the sulphate, chloride or hydroxide.

The formation of complex salts of glyphosate with metal ions has been noted, for example by Hensley et al, (*Weed Research* 18, 293–297 (1978)) and complex salts of glyphosate with iron (III) have been discussed by McBride et al in *Soil Sci. Soc. Am. J.* 53, 1668–1673. However, the effect does not seem to have been perceived as being useful or put to any industrial use. The structure of the complex salts is not completely clear but, in the case of iron (III), a complex salt is formed which appears to contain a 1:1 ratio of glyphosate and iron (III), which is insoluble in water and which appears to precipitate out of solution almost quantitatively at ambient temperature.

Once formed, the glyphosate-containing precipitate may be removed by any suitable method, some of the simplest and most effective methods being filtration and centrifugation. In order to assist the separation process, it may be an advantage to employ a flocculating surfactant at this stage. Suitable flocculating surfactants are well known and are readily available to those skilled in the art.

Thus, the process of the present invention allows glyphosate to be removed from the effluent from a glyphosate manufacturing process, and this can have extremely beneficial environmental effects since the release of glyphosate with the effluent can be prevented.

It is, of course, preferable from the point of view of the manufacturer if the glyphosate can be recovered from the precipitate and the present inventors have also devised a method for achieving this objective.

Once the precipitate of the complex glyphosate salt has been separated, it may be used to form an alkaline aqueous slurry. The raising of the pH causes the decomposition of the complex glyphosate salt to give a soluble glyphosate salt and when iron (III) is used as the counter-ion, the precipitation of iron (III) hydroxide or hydrated iron (III) oxide. Thus this process is particularly advantageous because it not only permits the recovery of glyphosate in a form which can be recombined with glyphosate produced in the manufacturing process, but it also ensures that the iron (III) which was originally used to precipitate the glyphosate is recovered in a form in which it can be converted to a soluble iron (III) salt and re-used in the effluent treatment process of the invention.

In general, the pH of the slurry will be greater than 8 but it is more usual for a higher pH, for example 12 or above, to be used. Typically, the slurry will have a pH of from about 12.2 to 12.8, often about 12.4.

The raising of the pH of the mixture causes the formation of iron (III) hydroxide or hydrated ferric oxide which can then be removed from the mixture by any appropriate method.

The slurry may be formed in two steps: firstly water may be added to the precipitate and mixed to form a slurry and, subsequently, a base may be added to the mixture.

In an alternative procedure, however, the glyphosate-containing complex salt may be added directly to an alkaline solution. Often this will have the advantage of giving a more concentrated glyphosate solution.

In either procedure, the slurry may be formed at ambient temperature.

Any base may be used to raise the pH of the solution but bases which result in the formation of a water soluble glyphosate salt are particularly suitable since the separation of the iron (III) hydroxide from the glyphosate is then made much easier. Examples of especially suitable bases include sodium and potassium hydroxide. In order to keep the amount of solution to a minimum, it is preferred that the base be relatively concentrated. Conveniently, the base will be a commercially available base, for example 50% w/w sodium hydroxide.

The iron (III) hydroxide can be removed from the mixture by a variety of known methods but a particularly appropriate one is centrifugation.

Once the iron (m) hydroxide has been removed from the process, the aqueous solution of the glyphosate salt can be recombined with the product from the main part of the process.

The process of the present invention may be operated either as a batch process or as a continuous process.

The invention will now be further illustrated by the following non-limiting examples.

EXAMPLE 1
Formation of a Complex Salt of Glyphosate by the Addition of Ferric Sulphate to a Glyphosate-Containing solution An aqueous solution (300 ml) containing 1% w/w phosphonomethylglycine and 20% w/w sodium chloride, with a total organic carbon content estimated to be 1310 mg/l was treated with 7.2g of a 50% w/w solution of ferric sulphate, the pH being held between 0.9 and 1.1 using sodium hydroxide solution. After removing the precipitate by filtration, the total organic carbon content of the liquors was found to be 60 mg/l.

EXAMPLE 2
Formation of a Complex Salt of Glyphosate by the Addition of Ferric Chloride to a Glyphosate-Containing Solution An aqueous solution as described in Example 1 above (300 ml) was treated with 7.7 g of a 50% w/w solution of ferric chloride hexahydrate, the pH of the slurry being maintained at 1.0 using sodium hydroxide solution. After removing the precipitate by filtration, the total organic carbon content of the filtrates was estimated to be 70 mg/l.

EXAMPLE 3
Recovery of Glyphosate

A typical process effluent containing N-phosphonomethylglycine (119.7 g at 1.35% w/w) was treated with an aqueous solution of ferric sulphate (9.0 g at 45% w/w), maintaining the pH at 4.0 by the addition of 47% sodium hydroxide solution. The resulting precipitate was filtered off and re-slurried with sodium hydroxide solution (38.4 g at 23.5% w/w), for one hour at pH 12.7. Removal of the gelatinous hydrated ferric oxide (ferric hydroxide) by filtration produced a pale yellow solution which was found by high performance liquid chromatography to contain 71.8% of the phosphonomethylglycine present in the original sample.

EXAMPLE 4
Recycle of Ferric Ions

The hydrated ferric oxide from Example 3 was charged to a further 120 g portion of process effluent at pH 1.3 together with fresh ferric sulphate solution (1.8 g at 45%), and used to precipitate phosphonomethylglycine from this solution.

Thus, the process of the present invention has the advantages that it ensures a high rate of recovery of glyphosate from a solution containing a soluble glyphosate salt and, particularly when an iron (III) salt has been used to precipitate the glyphosate, it allows high recovery of iron (III) which can then be recycled and re-used to recover more glyphosate. The process of the invention therefore provides an economical way of removing glyphosate from effluent in which it is present, which, unlike prior art processes, does not involve the use of expensive reagents or severe reaction conditions such as elevated temperature and pressure.

We claim:

1. A process for removing N-(phosphonomethylglycine) (glyphosate) or a salt or ionic form thereof from an aqueous mixture in which it is present, wherein the aqueous mixture is an effluent from a glyphosate manufacturing process, wherein the pH of the mixture is adjusted to from 1 to 4 the process comprising adding to the mixture of ions capable of forming an insoluble or partially soluble complex glyphosate salt, and removing the complex salt from the mixture.

2. A process as claimed in claim 1, wherein the ions are calcium, magnesium, aluminium or iron (III) ions.

3. A process as claimed in claim 2, wherein the ions are iron (III) ions and the pH of the glyphosate-containing mixture is adjusted before the addition of the iron (III) salt.

4. A process as claimed in claim 1, wherein the ions are added in the form of a salt which is soluble in aqueous solution at the pH of the glyphosate-containing mixture.

5. A process as claimed in claim 4, wherein the ion is iron (III) and the soluble salt is the sulphate, chloride or hydroxide.

6. A process as claimed in claim 1, wherein the precipitate is removed by filtration or centrifugation.

7. A process as claimed in claim 2 wherein the ions capable of forming an insoluble or partially soluble complex glyphosate salt are iron (III) ions, further comprising recovering glyphosate from the precipitate of complex salt by a process comprising forming an aqueous slurry of the precipitate having a pH greater than 8 and removing the resultant ferric hydroxide or hydrated ferric oxide from the slurry to give an aqueous solution containing glyphosate.

8. A process as claimed in claim 7, wherein the pH of the slurry is above about pH 12.

9. A process as claimed in claim 7, wherein the slurry is formed by adding water to the precipitate and subsequently adding a base or by adding the precipitate to an aqueous solution of base.

10. A process as claimed in claim 9, wherein the base is an alkali metal hydroxide.

11. A process as claimed in claim 1 in which the pH of the mixture is adjusted to about 3.

* * * * *